United States Patent [19]

Cordi et al.

[11] Patent Number: 5,468,763

[45] Date of Patent: * Nov. 21, 1995

[54] USE OF A GLYCINE B PARTIAL AGONIST FOR MEMORY AND LEARNING ENHANCEMENT OR TREATMENT OF A COGNITIVE DISORDER

[75] Inventors: Alex A. Cordi, St. Louis; Gail E. Handelmann, Chesterfield; Joseph B. Monahan, Black Jack, all of Mo.

[73] Assignee: G. D. Searle & Co., Chicago, Ill.

[ * ] Notice: The portion of the term of this patent subsequent to Feb. 11, 2009, has been disclaimed.

[21] Appl. No.: 975,298

[22] Filed: Nov. 12, 1992

Related U.S. Application Data

[63] Continuation of Ser. No. 727,175, Jul. 9, 1991, abandoned, which is a continuation of Ser. No. 438,494, Dec. 1, 1988, Pat. No. 5,087,633, which is a continuation-in-part of Ser. No. 127,121, Dec. 1, 1987, Pat. No. 4,904,681.

[51] Int. Cl.$^6$ .................................................. A61K 31/41
[52] U.S. Cl. ................................................ 514/380; 514/879
[58] Field of Search ...................................... 514/380, 879

[56] References Cited

PUBLICATIONS

The Merck Index, 11th ed., #2758, 1989.
The Physicians Desk Reference, 44th ed., pp. 1239–1240, 1990.

*Primary Examiner*—Kimberly R. Jordan
*Attorney, Agent, or Firm*—J. Timothy Keane

[57] ABSTRACT

A class of Glycine B partial agonists is described for use in memory and learning enhancement or for treatment of a cognitive disorder. Preferred Glycine B partial agonists include the compound D-cycloserine and its prodrug compounds.

6 Claims, 2 Drawing Sheets

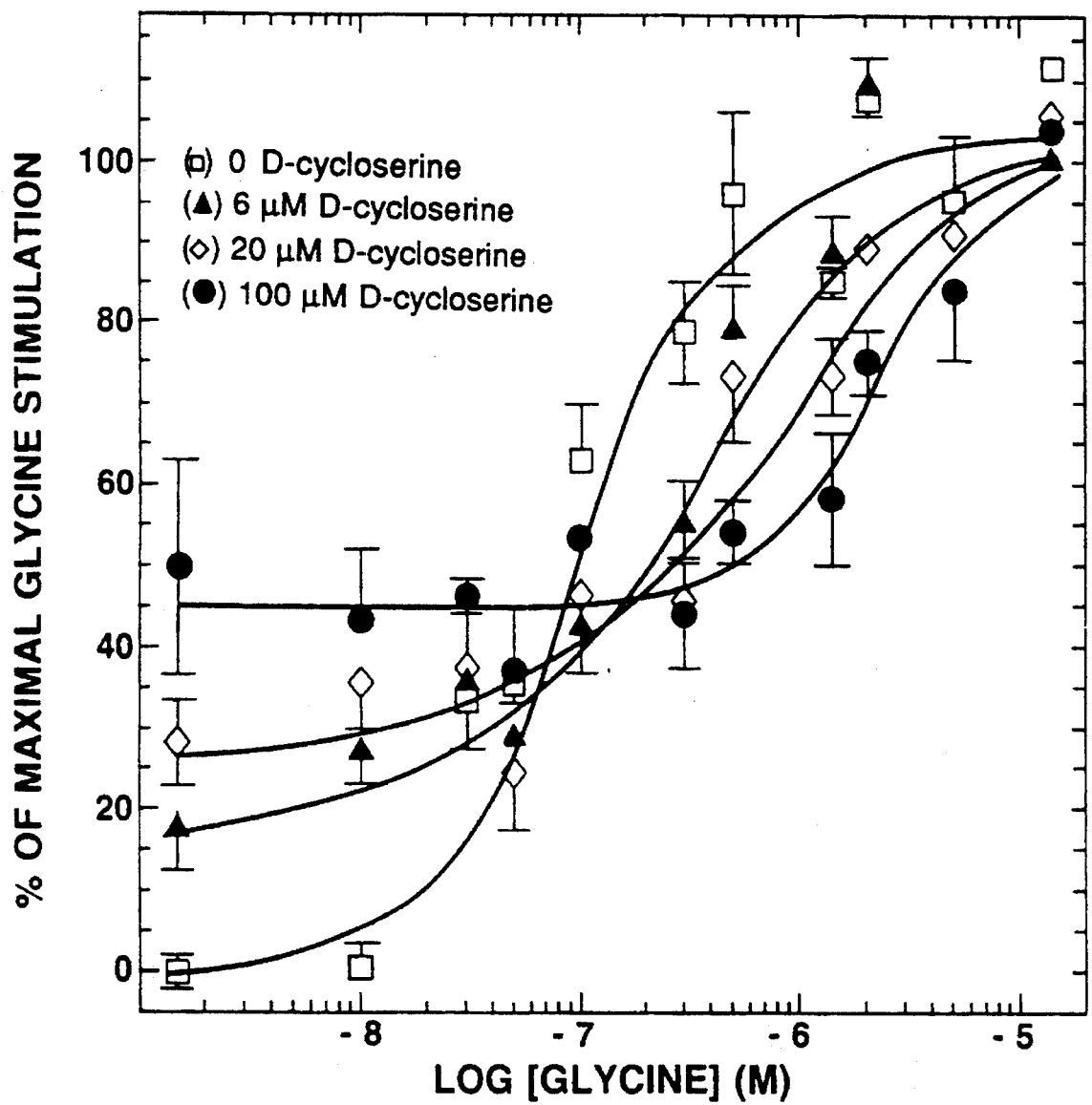

USE OF A GLYCINE B PARTIAL AGONIST FOR MEMORY AND LEARNING ENHANCEMENT OR TREATMENT OF A COGNITIVE DISORDER

This application is a continuation of U.S. application Ser. No. 07/727,175 filed 9 Jul. 1991, now abandoned, which is a continuation of U.S. application Ser. No. 07/438,494 filed 1 Dec. 1988, now issued as U.S. Pat. No. 5,087,633, which is a continuation-in-part of U.S. application Ser. No. 07/127,121 filed on 1 Dec. 1987, now issued as U.S. Pat. No. 4,904,681.

FIELD OF THE INVENTION

This invention is in the field of clinical neurology and relates specifically to compounds, formulations and methods for memory enhancement and for treatment of cognitive disorders.

BACKGROUND OF THE INVENTION

There are many memory-related conditions for which therapeutic treatments are under investigation, such as methods to enhance memory or to treat memory dysfunction. For example, memory dysfunction is linked to the aging process, as well as to neurodegenerative diseases such as Alzheimer's disease. Also, memory impairment can follow head trauma or multi-infarct dementia. Many compounds and treatments have been investigated which can enhance cognitive processes, that is, which can improve memory and retention.

The compound piracetam has been prescribed for treatment to enhance memory [Giurgea et al, *Arch. Int. Pharmacodyn. Ther.*, 166, 238 (1967)]. U.S. Pat. No. 4,639,468 to Roncucci et al describes the compound milacemide which is mentioned as useful for treatment of memory troubles. Further investigations of milacemide have documented the memory-enhancing capabilities of milacemide in human subjects [B. Saletu et al, *Arch. Gerontol. Geriatr.*, S, 165–181 (1986)].

Other compounds having effects on the Central Nervous System (CNS) have been investigated. For example, the compound D-cycloserine, in its D- and L-isomer forms, has been evaluated for effects on the upper region of the CNS [O. Mayer et al, *Arzneim. Forsch.*, 21(2), 298–303 (1971)]. These cycloserine isomers have also been evaluated for psychological and physiological effects in healthy human subjects [M. Vojtechovsky, *Act. Nerv. Super.*, 7(3), 269 (1965); V. Vitek et al, *Psychopharmacologia*, 7(3), 203–219 (1965)].

BRIEF DESCRIPTION OF FIGURES

FIG. 2 is a graph showing concentration of glycine influence on maximal glycine stimulation of TCP binding in the presence of various concentrations of D-cycloserine.

DESCRIPTION OF THE INVENTION

Figure 1:
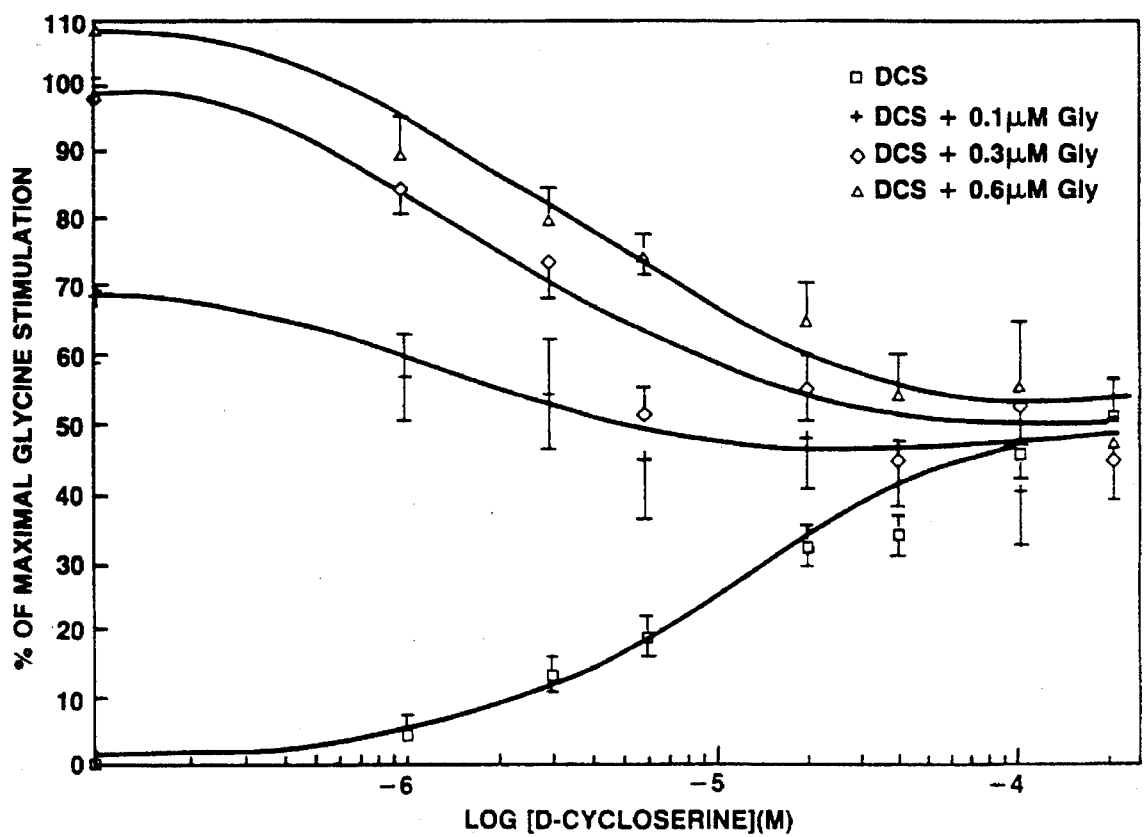
FIG. 1 is a graph showing concentration of D-cycloserine influence on maximal glycine stimulation of TCP binding in the presence of various concentrations of glycine.

Improvement of cognitive function or treatment of a cognitive dysfunction is achieved by treatment of an animal with a therapeutically-effective amount of a Glycine B partial agonist or a prodrug thereof. Such Glycine B partial agonist may be provided by one or more compounds selected from the family of compounds of Formula I:

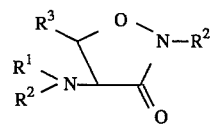

wherein $R^1$ is selected from hydrido, alkyl, haloalkyl, alkoxyalkyl, cycloalkyl, aralkyl and aryl; wherein $R^2$ is selected from hydrido, alkyl, aralkyl, aryl,

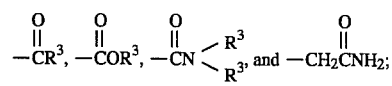

wherein '$R^1$ and $R^2$ may be taken together to form a Schiff-base derived group selected from derivatives of aldehydes and ketones; wherein $R^3$ is selected from hydrido, alkyl, haloalkyl, alkoxy, alkoxyalkyl, cycloalkyl, aralkyl and aryl; or a pharmaceutically-acceptable salt thereof. The phrase "improvement of cognitive function" embraces treatment to improve or enhance memory and treatment to address a cognitive deficit linked to a neurological disorder.

A preferred family of compounds consists of compounds wherein $R^1$ is selected from hydrido, lower alkyl, haloalkyl, cycloalkyl, alkoxyalkyl, phenalkyl and phenyl; wherein $R^2$ is selected from hydrido, lower alkyl, phenalkyl, phenyl,

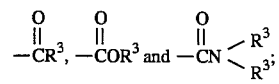

wherein the Schiff-base derived group is derived from acetylacetone, salicylaldehyde, benzophenone derivatives and acetylacetic acid esters; and wherein $R^3$ is selected from hydrido, lower alkyl and benzyl.

A more preferred group of compounds within Formula I consists of these compounds wherein $R^1$ is hydrido; wherein $R^2$ is selected from

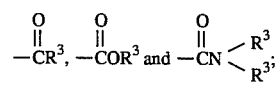

wherein the Schiff-base derived group is selected from

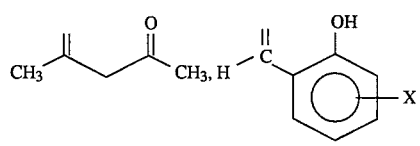

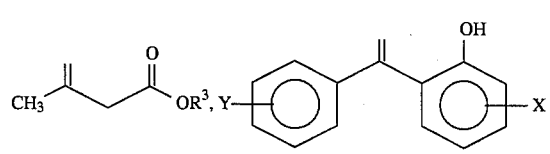

wherein each of X and Y is independently one or more groups selected from hydrido, lower alkyl and halo; and wherein $R^3$ is selected from hydrido, lower alkyl and phenyl.

A most preferred group of compounds within Formula I consists of those compounds wherein $R^1$ is selected from hydrido and the Schiff-base derived groups

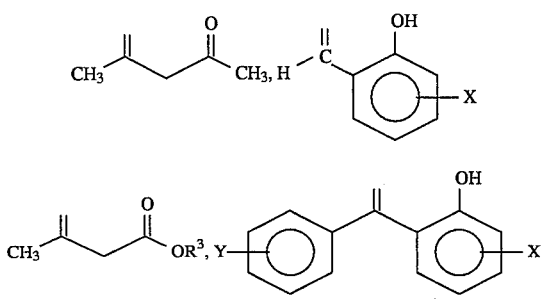

wherein each of X and Y is independently selected from fluoro, chloro and bromo; and wherein each of $R^2$ and $R^3$ is hydrido.

Most preferred of the compounds of Formula I is the compound 4-amino-3-isoxazolidone having the structural formula

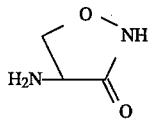

This compound exists in the L- and D-isomeric forms, of which the compound D-cycloserine is most highly preferred.

Also embraced by Formula I are the tautomeric forms of these compounds as represented by Formula II:

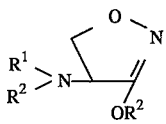 II wherein $R^1$, $R^2$ and $R^3$ are as defined for the compounds of Formula I.

The term "hydrido" denotes a single hydrogen atom (H) which may be attached, for example, to a carbon atom or attached to an oxygen atom to form an hydroxyl group. Where the term "alkyl" is used, either alone or within another term such as "haloalkyl", the term "alkyl" embraces linear or branched radicals having one to about twenty carbon atoms or, preferably, one to about ten carbon atoms. More preferred alkyl radicals are "lower alkyl" radicals having one to about five carbon atoms. The term "cycloalkyl" embraces cyclic radicals having three to about ten ring carbon atoms, preferably three to about five carbon atoms, such as cyclopropyl and cyclobutyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. Examples of a polyhaloalkyl are trifluoromethyl, 2,2,2-trifluoroethyl, perfluoroethyl and 2,2,3,3-tetrafluoropropyl groups. The terms "alkoxy" and "alkoxyalkyl" embrace linear or branched oxy-containing radicals having alkyl portions of one to about ten carbon atoms, such as methoxy group. The "alkoxy" or "alkoxyalkyl" radicals may be further substituted with one or more halo atoms, such as fluoro, chloro or bromo, to provide haloalkoxy or haloalkoxyalkyl groups. The term "aralkyl" is exemplified by "phenalkyl" of which benzyl is a specific example.

Specific examples of alkyl groups are methyl, ethyl, n-propyl, isopropyl, n-butyl, sec-butyl, iso-butyl, tert-butyl, n-pentyl, iso-pentyl, methylbutyl, dimethylbutyl and neopentyl.

Included within the family of compounds of Formulas I and II are the isomeric forms of the described compounds including diastereoisomers, and the pharmaceutically-acceptable salts thereof. The term "pharmaceutically-acceptable salts" embraces salts commonly used to form alkali metal salts and to form addition salts of free acids or free bases. Since the compounds of Formulas I and II contain basic nitrogen atoms, such salts are typically acid addition salts or quaternary salts. The nature of the salt is not critical, provided that it is pharmaceutically acceptable, and acids which may be employed to form such salts are, of course, well known to those skilled in this art. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. All of these salts may be prepared by conventional means by reacting, for example, the appropriate acid or base with the corresponding compound of Formulas I and II.

The term "prodrug", as used herein, embraces compounds which are precursors of Glycine B partial agonists. Such precursor compounds can release the Glycine B partial agonist by some chemical or enzymatic reaction taking place in the body or, optimally, in the brain.

Compounds of Formula I and Formula II can be synthesized by methods described in the literature. For example, syntheses of N-acyl derivatives and Schiff-base derivatives of D-cycloserine are described by N. P. Jensen et al, *J. Med. Chem.*, 23 6–8 (1980). Syntheses of N,N'-diacyl derivatives of cycloserine are described by J. C. Howard, *J. Org. Chem.*, 46, 1720–1723 (1981). Syntheses of alkyl derivatives of cycloserine are described by C. H. Stammer, *J. Med. Chem.*, 13(6), 1013 (1970). Syntheses L- and D-isomers of cycloserine, as well as analogues thereof, are described by Pl. A. Plattner et al, *Aelv. Chim. Acta.*, 40, 1531 (1957).

BIOLOGICAL EVALUATION

Glycine Binding Assay Procedure

Synaptic plasma membranes (SPM) were prepared from rat forebrain and stored as previously described [J. B. Monahan and J. Michel, *J. Neurochem.*, 48, 1699–1708 (1987)]. Frozen membranes were thawed and diluted 1:20 with 0.04% triton X-100 in 50 mM tris/acetate (pH 7.4). Following incubation at 37° C. for 30 min., the SPM were collected by centrifugation at 95,000×g for 15 min. The pellet was resuspended in 50 mM tris/acetate (pH 7.4, triton-free) and hand-homogenized five times. The membranes were again centrifuged as above. The pellet was washed two additional times with 50 mM tris/acetate (without homogenization) and centrifuged. The final pellet was resuspended with homogenization in 50 mM tris/acetate.

In the general receptor binding assay procedure, 10 nM [$^3$H]glycine was added to the appropriate concentration of the test compounds and the assay initiated by the addition of 0.2–0.4 mg of ice cold SPM. The assay, which was done in 1.5 ml centrifuge tubes, was adjusted to a total volume of 1.0 ml with all additions being made in 50 mM tris/acetate, pH 7.4 at 4° C. After a 10 minute incubation at 2° C., the samples were centrifuged for 15 min. at 12,000 g (4° C.) in a Beckman Microfuge 12. The supernatant was aspirated and the tube tip containing the pelleted membranes cut off and agitated in 0.5 ml of Beckman BTS-450 tissue solubilizer for a minimum of 6 hours at room temperature. Beckman MP scintillation cocktail (5 ml) containing 7 ml/liter acetic acid was then added and the samples counted on a Beckman LS 5800 liquid scintillation counter with automatic corrections for quenching and counting efficiency. Nonspecific binding was defined as the residual binding in the presence of 0.1 mM glycine and usually amounted to 25–35% of the total binding. The binding of [$^3$H]glycine to the SPM was analyzed using Scatchard and Hill transformations and the $K_i$ for other compounds was determined using logit-log analysis. Calculations and regression analysis were performed using templates developed for Lotus 123 as previously described.

| Result | $K_i$ (μM) |
| --- | --- |
| Glycine | 0.18 |
| D-cycloserine | 1.92 |
| L-cycloserine | >100 |

TCP Modulation Assay

[$^3$H]TCP binding was performed using Triton X-100 washed synaptic plasma membranes (SPM) prepared from rat forebrain (30–45 day old, male Sprague-Dawley; Sasco, St. Charles, Mo.) as described previously [J. W. Thomas, W. F. Hood, J. B. Monahan, P. C. Contreras and T. L. O'Donohue, *Brain Res.*, 442, 396–398 (1988)]. The assay was initiated by the addition of SPM (0.15–0.25 mg) to an incubation containing 2.0 nM [$^3$H]TCP (47.1 Ci/mmole; New England Nuclear, Boston, Mass.) and varous concentrations of the appropriate test compound in a total volume of 0.5 ml (all additions were made in 5 mM Tris/HCl buffer, pH 7.4) and continued for 60 min at 25° C. The samples were then filtered through glass fiber filters (Schleicher and Schuell #32) which were pretreated with 0.05% (v/v) polyethylenimine. The filters were washed and the radioactivity quantitated by liquid scintillation spectrometry. Stimulation of [$^3$H]TCP binding was measured as an increase in basal specific binding (basal binding=2583±381 DPM and this value increased to a maximum of 4712±779 DPM in the presence of 0.6 μM glycine) with nonspecific binding as the residual binding in the presence of 60 μM PCP (562±30 DPM). The $K_d$ for [$^3$H]TCP under basal conditions was 44 nM. The $EC_{50}$ values for the stimulation of [$^3$H]TCP binding were determined using a four parameter logistic regression analysis.

D-Cycloserine stimulates basal [$^3$H]TCP binding in a dose dependent manner with an $EC_{50}$=19.7 μM. Previous data show that D-cycloserine interacts with the NMDA-associated [$^3$H]glycine recognition site ($K_i$=2.33±0.29 μM). No affinity for the NMDA recognition site, however, was detected as evidenced by the lack of displacement of NMDA-specific L-[$^3$H]glutamate binding ($K_i$>100 μM). This finding indicates that D-cycloserine enhances [$^3$H]TCP binding through its interaction with the NMDA receptor-associated glycine recognition site (herein defined as the "Glycine B receptor"). The maximal stimulation produced by D-cycloserine, however, was significantly less than that produced by both glycine and D-serine.

This apparent lower efficacy indicates the potential partial agonist character of D-cycloserine which was confirmed by the following experiment. As shown in FIG. 1, in the absence of exogenously added glycine, D-cycloserine has agonist properties and stimulates [$^3$H]TCP binding to a maximum of 40–50% of the stimulation induced by glycine alone. However, in the presence of various concentrations of glycine (0.1–0.6 μM), D-cycloserine has an apparent antagonist character and reduces the maximal level of glycine stimulation. These data provide a family of D-cycloserine dose-response curves (generated in the presence of several fixed concentrations of glycine) which asymptotically approach 40–50% of the maximal stimulation induced by glycine alone, a pattern characteristic of compounds with partial agonist properties as is known with different compounds acting on other receptors.

Further confirmation of the partial agonist character of D-cycloserine was demonstrated in experiments wherein a glycine dose-response analysis was performed in the presence of several fixed concentrations of D-cycloserine (0–100 μM). As shown in FIG. 2, D-cycloserine potentiated the glycine stimulation of [$^3$H]TCP binding at glycine concentrations below 0.1 μM, while at higher glycine concentrations (0.1–15 μM) D-cycloserine produced a rightward shift in the dose-response curve. These results are again consistent with partial agonist characteristics.

The functional analysis of D-cycloserine described herein is the first report of a compound interacting at this glycine modulatory site exhibiting partial agonist characteristics. These results along with the favorable brain bioavailability of the compound and evidence for involvement of the NMDA receptor in learning and memory potentially make D-cycloserine a valuable tool to probe NMDA receptor function. More importantly, Glycine B partial agonists would be expected to provide therapeutic benefits in treatment of cognitive dysfunctions, such as Alzheimer's Disease, age-associated memory impairment, multi-infarct dementia, mixed organic brain syndrome metabolic encephalopathies of various origins, alcoholic dementia and various learning disorders. In particular, the Glycine B partial agonist compounds would be useful in treatment of Alzheimer's Disease, age-associated memory impairment and learning deficit, in human subjects suffering from such disorders, as well as for use in improvement of memory and learning ability in healthy individuals.

PASSIVE AVOIDANCE ASSAY METHODS

Subjects: Male Long-Evans rats weighing about 200 g (Sasco) were used. They were housed two per cage with ad lib food and water for the duration of the experiment.

Apparatus: The apparatus consisted of a plexiglass box (32×26×20 cm) with a lid with a floor of metal rods spaced 1.8 cm apart. The box was divided into two chambers, one painted black and the other gray. Two doors (12 cm high) were cut into the front of the box allowing access into each chamber.

A Y-shaped plexiglas runway was attached to the front of the box. The stem of the Y was 16 cm long and unpainted.

The arms of the Y (14 cm long each) led to the two doors and each was painted the color of the chamber to which it led. The stem of the Y extended over the edge of the table on which the apparatus was placed, so that it was approximately 75 cm above the floor. The metal floor of the box was wired to a Lafayette shock generator so that a 0.5 mAmp shock could be delivered.

Procedure: On the first test day, each rat was placed on the runway and allowed to enter one of the chambers. The door to this chamber was then closed, and the rat was then allowed to enter the other chamber. On the second test day, some of the rats were given i.p. injections of either D-cycloserine dissolved in 0.9% saline, or saline alone. Sixty minutes later, each rat was again allowed to enter one chamber, where it received a footshock for 2 seconds. If the rat did not previously receive an injection, it was injected with either D-cycloserine or saline ten seconds after the footshock. On the third test day, the rat is again placed on the runway and allowed to enter a chamber. On days two and three, each rat's latency to enter a chamber, and which chamber it entered, are recorded.

Effects of D-cycloserine (10 mg/kg i.p. ) on passive avoidance learning latency (secs.) to enter box 24 hours after shock are shown in Table I.

TABLE I

| | Time of Drug Treatment | |
|---|---|---|
| | Before Shock | After Shock |
| Saline | 8.9 ± 1.5 (n = 6) | 14.8 ± 3.1 (n = 5) |
| D-cycloserine | 16.6 ± 3.0 (n = 6) | 22.8 ± 2.4 (n = 6) |

In this animal model for demonstrating memory enhancement, the delay in time for the rat to enter the chamber (the "latency period") is a measure of the rat's memory of the previous experience in receiving a foot shock. The longer is the latency period, the better is the memory enhancing effect of the tested compound. Those animal experiments show that D-cycloserine acting as a glycine ligand has memory-enhancing effect which is characterized in this model by an increased latency for the animal to enter the compartment.

The dose-effect relationship of D-cycloserine, as well as the effect of this compound when administered just before the information retrieval trial, were also studied, as reported in Table II.

TABLE II

| | % of Saline Control Latency in Passive Avoidance | | |
|---|---|---|---|
| Dose of DCS | Administration | | |
| (mg/kgi.p.) | pre-shock (%) | post-shock (%) | pre-retrieval (%) |
| Saline | 100 | 100 | 100 |
| 0.3 | 152* | 160* | 105 |
| 3 | 245* | 215* | 153* |
| 10 | 138* | 153* | 180* |
| 20 | | | 100 |

*Statistically different from control (P < 0.05, t-test)

Rewarded Alternation of Rats in a T-maze

Rats were trained on a place learning task in a T-maze following i.p. administration of D-cycloserine (3 mg/kg) or saline. Both groups learned the task in about 20 trials. Learning is defined as making 9 correct out of 10 consecutive choices. On the following day, the food reward was placed in the other arm of the maze (reversal). The saline-treated rats required about 32 trials to learn the reversal, while the D-cycloserine rats learned the reversal in about 20 trials. These data confirm in this behavioral paradigm that D-cycloserine has a facilitating effect on processes of learning and memory.

Intact hippocampal structure is necessary for the brain to process information and store it in memory. The phenomenon of "long term potentiation" (LTP) seems to be the mechanism by which this process occurs. The leading role of the N-methyl-D-aspartate ("NMDA") receptor, a sub-type of excitatory amino acid receptor, in LTP has been firmly established by electrophysiological studies. NMDA antagonists such as 2-amino-7-phosphonoheptanoic acid (APH) inhibit the establishment or propagation of LTP.

Recently, it has been demonstrated in neurophysiological studies that glycine potentiates the response to activation of NMDA receptors in cultured brain neurons. This is a strychnine-insensitive action and it is postulated to result from activation of a supraspinal glycine receptor (herein defined as the Glycine B receptor) which modulates the opening of the Na+-Ca++ channel triggered by NMDA activation. For example, milacemide, as a glycine prodrug, increases the whole brain content of glycine by 30%. By the mechanism explained above, this increase of glycine can lead to a facilitation of NMDA transmission and improved memory and learning ability.

Data presented in Table II demonstrate that the dose-effect relationship of D-cycloserine is characterized by a bell-shaped curve. The unusual relationship is believed to be associated with the partial agonist character of D-cycloserine. It is apparent, therefore, that maximum efficacy will be achieved within a defined range and that higher doses e.g., greater than 500 mg per dose in human subjects, would be expected to result in reduced efficacy.

The acidic amino acids, aspartic and glutamic acid, have been found to possess both excitatory and excitotoxic properties [J. W. Olney, Science, 164, 719–721 (1969); J. W. Olney et al., Exp. Brain Res., 14, 61–76 (1971)]. Indeed, neurons which have excitatory amino acid receptors on their dendritic or somal surfaces undergo acute excitotoxic degeneration when these receptors are excessively activated by glutamic acid.

Glycine agonists which have a potentiating effect on the NMDA transmission would be expected to increase the glutamic acid excitotoxicity. A Glycine B partial agonist achieves beneficial excitatory effects without the detrimental excitotoxic side effect.

Most glycine ligands are very polar molecules and hardly cross the blood brain barrier. Because of the difficulty in crossing the blood brain barrier, such ligands are not bioavailable at concentrations effective to be therapeutically beneficial.

It is known that D-cycloserine easily passes the blood brain barrier [Goodman and Gilman, The Pharmacologic Basis of Therapeutics, Ch., 53, 1210–1211 (1980)].

It was surprising and unexpected that D-cycloserine was found to have such a good affinity for the strychnine-insensitive glycine receptor as shown by the binding data above. Glycine agonists are believed to facilitate NMDA transmission and, therefore, to have a positive effect on LTP. The improvement in LTP is postulated to be linked to memory enhancement.

Administration of compounds within Formulas I and II to humans can be by any technique capable of introducing the compounds into the bloodstream of a human patient, including oral administration, and by intravenous, intramuscular and subcutaneous injections.

Compounds indicated for prophylactic therapy will preferably be administered in a daily dose generally in a range from about 0.1 mg to about 10 mg per kilogram of body weight per day. A more preferred dosage will be a range from about 0.2 mg to about 5 mg per kilogram of body weight. Most preferred is a dosage in a range from about 0.3 to about 2.5 mg per kilogram of body weight per day. A suitable dose can be administered in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The active compound is usually administered in a pharmaceutically-acceptable formulation. Such formulations may comprise the active compound together with one or more pharmaceutically-acceptable carriers or diluents. Other therapeutic agents may also be present in the formulation. A pharmaceutically-acceptable carrier or diluent provides an appropriate vehicle for delivery of the active compound without introducing undesirable side effects. Delivery of the active compound in such formulations may be by various routes including oral, nasal, topical, buccal and sublingual, or by parenteral administration such as subcutaneous, intramuscular, intravenous and intradermal routes.

Formulations for oral administration may be in the form of capsules containing the active compound dispersed in a binder such as gelatin or hydroxypropylmethyl cellulose, together with one or more of a lubricant, preservative, surface-active or dispersing agent. Such capsules or tablets may contain a controlled-release formulation as may be provided in a disposition of active compound in hydroxypropylmethyl cellulose.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A method to improve cognitive function or to treat cognitive dysfunction in a subject in need thereof, which method comprises administering to the subject a thereapeutically-effective amount of a Glycine B partial agonist.

2. The method of claim 1 wherein said cognitive function is memory.

3. The method of claim 1 wherein said cognitive function is learning.

4. The method of claim 1 wherein said cognitive dysfunction is Alzheimer's Disease.

5. The method of claim 1 wherein said cognitive dysfunction is age associated memory impairment.

6. The method of claim 1 wherein said cognitive dysfunction is a learning deficit.

* * * * *